United States Patent [19]
Klaveness

[11] Patent Number: 5,639,444
[45] Date of Patent: Jun. 17, 1997

[54] METHOD OF ELECTRICAL IMPEDANCE IMAGING USING A TRIIODOPHENYL COMPOUND OR GAS ENCAPSULATED MICROBUBBLES

[75] Inventor: Jo Klaveness, Oslo, Norway

[73] Assignee: Nycomed Imaging AS, Oslo, Norway

[21] Appl. No.: 244,905

[22] PCT Filed: Jan. 4, 1993

[86] PCT No.: PCT/EP93/00006

§ 371 Date: May 4, 1995

§ 102(e) Date: May 4, 1995

[87] PCT Pub. No.: WO93/12717

PCT Pub. Date: Jul. 8, 1993

[30] Foreign Application Priority Data

Jan. 3, 1992 [GB] United Kingdom ............ 9200065

[51] Int. Cl.⁶ .................................................. A61B 5/055
[52] U.S. Cl. ............ 424/9.321; 424/9.37; 424/450; 514/974; 128/653.4; 436/173
[58] Field of Search .................. 424/9.31, 9.45, 424/9.454, 9.455, 9.52, 450, 9.321, 9.37; 423/328; 514/974; 436/173; 128/653.4, 654

[56] References Cited

U.S. PATENT DOCUMENTS

| | | | |
|---|---|---|---|
| 2,895,988 | 7/1959 | Archer et al. | 424/9.45 |
| 3,576,871 | 4/1971 | Hebky et al. | 424/9.45 |
| 4,442,843 | 4/1984 | Rasor et al. | 424/9.52 |
| 4,647,447 | 3/1987 | Gries et al. | 424/9.363 |
| 4,873,075 | 10/1989 | Counsell et al. | 424/1.1 |
| 4,880,008 | 11/1989 | Lauffer | 424/9.363 |
| 5,122,363 | 6/1992 | Balkus, Jr. et al. | 424/9.31 |
| 5,465,730 | 11/1995 | Zadehkoochak et al. | 128/734 |

FOREIGN PATENT DOCUMENTS

| | | |
|---|---|---|
| WO-A-87 02893 | 5/1987 | WIPO . |
| WO-A-88 00060 | 1/1988 | WIPO . |
| WO-A-89 11873 | 12/1989 | WIPO . |
| WO-A-91 19454 | 12/1991 | WIPO . |
| WO-A-92 10213 | 6/1992 | WIPO . |

Primary Examiner—Gary E. Hollinden
Attorney, Agent, or Firm—Bacon & Thomas

[57] ABSTRACT

Agents for use in improving tissue/tissue contrast in electrical impedance tomography are described. In particular triiodophenyl compounds, metal chelates, magnetic particles, conducting particles and microbubbles may be used.

5 Claims, 1 Drawing Sheet

A.C. circuit for the four-electrode method
G= Signal generator    V= A.C. voltage meter
S= Sample holder    DA= Differential amplifier
FC= Frequency counter

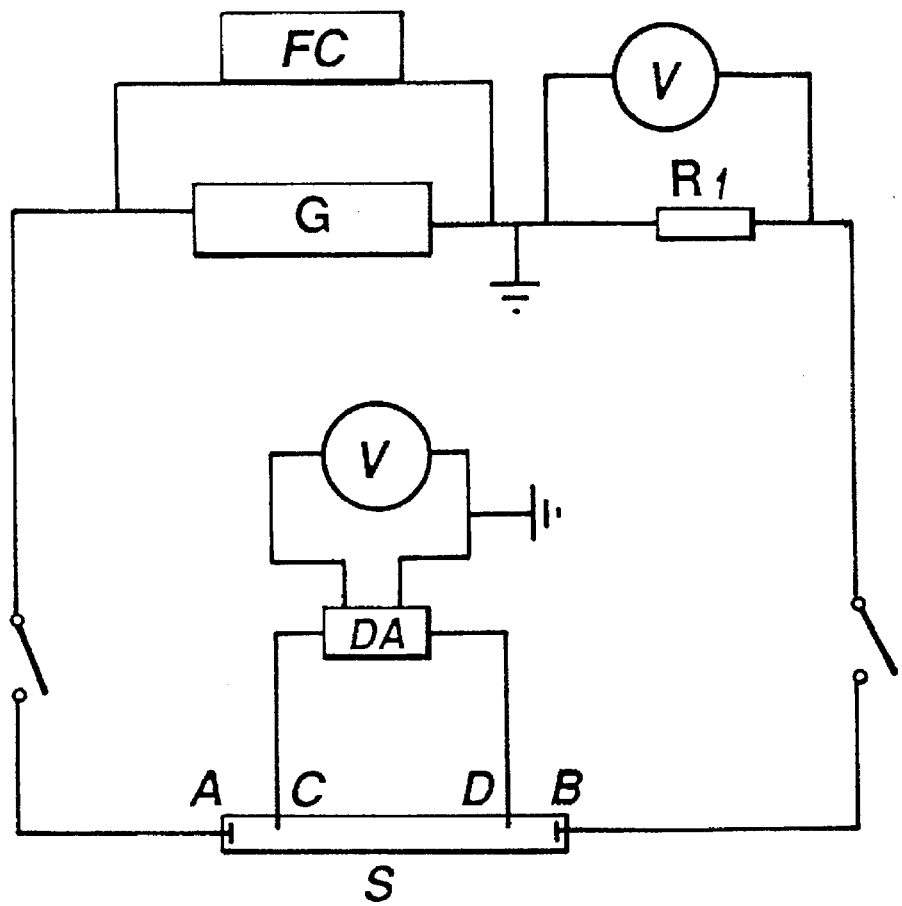
Fig.1: A.C. circuit for the four-electrode method
G= Signal generator    V= A.C. voltage meter
S= Sample holder    DA= Differential amplifier
FC= Frequency counter

METHOD OF ELECTRICAL IMPEDANCE IMAGING USING A TRIIODOPHENYL COMPOUND OR GAS ENCAPSULATED MICROBUBBLES

This application is a 371 of PCT/EP93/00006 filed Jan. 4, 1993, WO93/12717, Jul. 8, 1993.

This invention relates to the use of contrast media in electrical impedance imaging.

Electrical impedance imaging (EII), also referred to as electrical impedance tomography and applied potential tomography, is a medical imaging technique that was brought to a practical level during the 1980's, in particular by the Sheffield group of B H Brown, D C Barber et al.

The technique involves generation of images indicative of spatial, and if desired temporal, variations in electrical impedance or resistivity; images which, when of human or animal subjects, can provide information about the structure and functioning of the imaged tissues. The technique is attractive as a medical diagnostic tool since it is non-invasive and does not involve exposing the patient to potentially harmful ionizing radiation, it does not require the administration of radioactive species and it does not require the generation of strong, highly uniform magnetic fields.

In the version of EII developed by Brown, Barber et al., an array of evenly spaced electrodes is attached to the body about the region of interest, a very low alternating current is applied successively between adjacent pairs of electrodes and the potential difference between all other pairs is determined. Image construction is effected using a back projection technique.

Alternative approaches to data collection do exist and are described in the literature.

Thus for example reference may be made to Seagar et al. IEE Proceedings 134.A.:201–210 (1987), Barber et al. J. Phys. E. 17:723–733 (1984), Harris et al. Clin. Phys. Physiol. Meas. 8A:155–165 (1987), Brown et al. Clin. Phys. Physiol. Meas. 6:109–121 (1985), GB-A-2160323 (University of Sheffield), GB-A-2119520, WO-A-89/09564, WO-A-91/19454, Price IEEE Transactions on Nuclear Science NS-26:2736–2739 (1979), Webster et al. Clin. Phys. Physiol. Meas. 9A:127–130 (1988) and Kim et al. J. Microwave Power 18:245–257 (1983) and the documents cited therein.

Spatial variations revealed in electrical impedance (EI) images may result from variations in impedance between healthy and non-healthy tissues, variations in impedance between different tissues and organs or variations in apparent impedance due to anisotropic effects resulting for example from muscle alignment. Thus for example the difference in impedance between body fat and muscle tissue is such that the two should be differentiable in static EI images. Dynamic imaging techniques may be used to follow gastric emptying, heart and lung function and the like.

Static imaging is problematic insofar as the current image reconstruction techniques require a homogeneous reference data set—this can be calculated if an electrode array of known dimensions and spacings is used or if a data set is collected for a homogeneous reference sample of the same dimensions as the subject being imaged (e.g. a saline filled cast of the subject under investigation).

For dynamic imaging the problem does not arise as a data set collected before (or after) the event to be imaged may be used as the reference data set. The in vivo imaging reported thus far has concentrated heavily on dynamic imaging with the imaged event generally being the operation of a natural function such as breathing, gastric emptying, blood flow or heart function. In the first and last cases the reference data set may be chosen as the data set at one limit of the natural cycle, e.g. at maximum expiration, in the second the data set for a slice through the stomach before or after administration of a meal (e.g. water, saline, soup, "Oxo" or mashed potato) and in the third the data set before natural or artificial modification of blood flow (e.g. on haemorrhage, or by increasing the total blood volume by injection of relatively large quantities of isotonic saline, or by venous occlusion). In the case of gastric emptying, it has been found (see Avill et al. Gastroenterology 92:1019–1026 (1987)) that results are improved if natural variations of gastric pH are suppressed by administration of cimetidine. Avill et al. separately confirmed the importance of stabilizing gastric pH by demonstrating the variation in the EII signal strength that resulted from administration of pentagastrin, a stimulant of gastric acid secretion.

Thus, on the whole, EII has tended to be used in medical imaging to study natural events in which organ impedance changes occur (e.g. breathing, eating, blood flow, heart beating etc) with imaging optionally being assisted by artificially increasing the volume or fluid content of the organ under study, e.g. by administration of a meal, by increasing total blood volume, etc. Unlike diagnostic imaging modalities such as X-ray, MRI, ultrasound and scintigraphy however, there has as yet been no suggestion that EII might benefit from the use of contrast media, and in particular the use of parenterally administered contrast media, to improve organ or tissue contrast.

We now therefore propose the use in diagnostic EII of EII contrast agents, that is to say materials which on administration will serve to enhance contrast in the resulting images by modifying the impedance in those tissues, organs or ducts into which they distribute. Where such contrast agents serve to increase local impedance they will function as negative contrast agents and where they reduce local impedance they will function as positive contrast agents.

BRIEF DESCRIPTION OF THE DRAWING

FIG. 1 schematically illustrates the four-electrode method used for resistivity measurements.

Such contrast media may be administered enterally or, particularly preferably, parenterally and insofar as parenteral agents are concerned there is particular scope for improvement in both target-specificity and biotolerability relative to saline (which was used by Barber et al. (supra) to increase overall blood volume rather than as a contrast medium capable of iteself being visualized).

Thus in one aspect the invention provides a method of electrical impedance imaging of a human or animal, preferably mammalian, subject which method comprises parenterally administering to said subject an EII contrast agent, other than isotonic saline, and generating an electrical impedance image of at least part of said subject.

Viewed from another aspect the invention provides the use of a physiologically tolerable material, other than sodium chloride, which is capable on dispersion in water of yielding a fluid having an electrical impedance different from that of water, for the manufacture of a contrast medium for use on parenteral administration in a method of electrical impedance imaging.

A wide range of materials can be used as parenteral EII contrast agents but particular mention should be made of five categories of contrast agent: ionic materials; relatively low molecular weight non-ionic materials; site-specific materials; particulate materials; and relatively high molecular weight non-ionic or substantially non-ionic materials. (It is of course possible for one material to belong to more than one of these categories).

Insofar as ionic materials are concerned, particular mention should be made of the ionic materials already proposed in the literature for use as X-ray and MRI contrast agents. Examples of such materials include many compounds with extremely low toxicity even compared with saline, and compounds may be selected which distribute preferentially within the body, e.g. which congregate at particular tissues, organs or tissue abnormalities or which are essentially confined to the circulatory system and act as blood pool agents. Examples of ionic X-ray contrast agents suited for use according to the present invention include in particular the iodinated contrast agents, especially those containing one or more, generally one or two, triiodophenyl groups in their structure. The counterion for any ionic EII contrast agent should itself be physiologically tolerable and in this regard particular mention should be made of alkali and alkaline earth metal cations and cations deriving from organic bases, especially sodium, zinc and ammonium ions, and more especially lysine, calcium and meglumine.

Particular ionic X-ray contrast agents useful according to the invention thus include physiologically acceptable salts of 3-acetylamino-2,4,6-triiodobenzoic acid, 3,5-diacetamido-2,4,6-triiodobenzoic acid, 2,4,6-triiodo-3,5-dipropionamido-benzoic acid, 3-acetylamino-5-((acetylamino)methyl)-2,4,6-triiodobenzoic acid, 3-acetylamino-5-(acetylmethylamino)-2,4,6-triiodobenzoic acid, 5-acetamido-2,4,6-triiodo-N-((methylcarbamoyl) methyl)-isophthalamic acid, 5-(2-methoxyacetamido)-2,4,6-triiodo-N-[2-hydroxy-1-(methylcarbamoyl)-ethyl]-isophthalamic acid, 5-acetamido-2,4,6-triiodo-N-methylisophthalamic acid, 5-acetamido-2,4,6-triiodo-N-(2-hydroxyethyl)-isophthalamic acid, 2-[[2,4,6-triiodo-3[(1-oxobutyl)-amino]phenyl]methyl]butanoic acid; beta-(3-amino-2,4,6-triiodophenyl)-alpha-ethyl-propanoic acid, 3-ethyl-3-hydroxy-2,4,6-triiodophenylpropanoic acid, 3-[[(dimethylamino)-methyl]amino]-2,4,6-triiodophenyl-propanoic acid (see Chem. Ber. 93:2347 (1960)), alpha-ethyl-(2,4,6-triiodo-3-(2-oxo-1-pyrrolidinyl)- phenyl)-propanoic acid, 2-[2-[3-(acetylamino)-2,4,6-triiodophenoxy]ethoxymethyl]butanoic acid, N-(3-amino-2, 4,6-triiodobenzoyl)-N-phenyl-β-aminopropanoic acid, 3-acetyl-(3-amino-2,4,6-triiodophenyl)amino]-2- methyl-propanoic acid, 5-[(3-amino-2,4,6-triiodophenyl) methylamino]-5-oxypentanoic acid, 4-[ethyl-[2,4,6-triiodo-3-(methylamino)phenyl]amino]-4-oxo-butanoic acid, 3,3'-oxybis[2,1-ethanediyloxy-(1-oxo-2,1-ethanediyl)imino]bis-2,4,6-triiodobenzoic acid, 4,7,10,13-tetraoxahexadecane-1, 16-dioyl-bis(3-carboxy-2,4,6-triiodoanilide), 5,5'-(azelaoyldiimino)-bis[2,4,6-triiodo-3-(acetylamino)methyl-benzoic acid, 5,5'-(apidoldiimino)bis(2,4,6-triiodo-N-methyl-isophthalamic acid), 5,5'-(sebacoyl-diimino)-bis(2, 4,6-triiodo-N-methylisophthalamic acid), 5,5-[N,N-diacetyl-(4,9-dioxy-2,11-dihydroxy-1,12-dodecanediyl) diimino]bis(2,4,6-triiodo-N-methylisophthalamic acid), 5,5'5"-(nitrilo-triacetyltriimino)tris (2,4,6-triiodo-N-methyl-isophthalamic acid), 4-hydroxy-3,5-diiodo-alpha-phenylbenzenepropanoic acid, 3,5-diiodo-4-oxo-1(4H)-pyridine acetic acid, 1,4-dihydro-3,5-diiodo-1-methyl-4-oxo-2,6-pyridinedicarboxylic acid, 5-iodo-2-oxo-1(2H)-pyridine acetic acid, and N-(2-hydroxyethyl)-2,4,6-triiodo-5-[2-[2,4,6-triiodo-3-(N-methylacetamido)-5-(methylcarbomoyl)benzamino]acetamido]-isophthalamic acid, as well as other ionic X-ray contrast agents proposed in the literature e.g. in J. Am. Pharm. Assoc., Sci Ed. 42:721 (1953), CH-A-480071, JACS 78:3210 (1956), DE-A-2229360, U.S. Pat. No. 3,476,802, Arch. Pharm. (Weinheim, Ger) 306:11 834 (1973), J. Med. Chem. 6:24 (1963), FR-M-6777, Pharmazie 16:389 (1961), U.S. Pat. No. 2,705,726, U.S. Pat. No. 2,895,988, Chem. Ber. 93:2347 (1960), SA-A-68/01614, Acta Radiol. 12:882 (1972), GB-A-870321, Rec. Trav. Chim. 87:308 (1968), East German Patent 67209, DE-A-2050217, DE-A-2405652, Farm Ed. Sci. 28:912 (1973), Farm Ed. Sci. 28:996 (1973), J. Med. Chem. 9:964 (1966), Arzheim.-Forsch 14:451 (1964), SE-A-344166, U.S. Pat. No. 1,993,039, Ann 494:284 (1932), J. Pharm. Soc. (Japan) 50:727 (1930), and U.S. Pat. No. 4,005,188. The disclosures of these and all other documents cited herein are incorporated herein by reference.

Besides ionic X-ray contrast agents, such as those mentioned above, one may advantageously use as EII contrast agents the ionic compounds (such as for example GdDTPA and GdDOTA) which have been proposed for use as MRI contrast agents, especially the salts of paramagnetic metal complexes (preferably chelate complexes) with physiologically compatible counterions, as well as similar complexes in which the complexed metal ion is diamagnetic (as paramagnetism is not a property required for the EII contrast agent to function as such). Preferred complexed paramagnetic metal ions will include ions of Gd, Dy, Eu, Ho, Fe, Cr and Mn and preferred non paramagnetic complexed ions will include ions of Zn, Bi and Ca.

The complexing agent will preferably be a chelating agent such as a linear, branched or cyclic polyamine or a derivative thereof, e.g. a polyaminocarboxylic acid or a polyaminopolyphosphonic acid or a derivative of such an acid, e.g. an amide or ester thereof. Particular mention in this regard may be made of DTPA, DTPA-bisamides (e.g. DTPA-bismethylamide and DTPA-bismorpholide), DTPA-bis (hydroxylated-amides), DOTA, DO3A, hydroxypropyl-DO3A, TETA, OTTA (1,4,7-triaza-10-oxacyclododecanetricarboxylic acid), EHPG, HIDA, PLED, DCTA and DCTP as well as the other chelating agents mentioned in the literature, e.g. in U.S. Pat. No. 4,647,447, WO-A-86/02841, EP-A-130934, U.S. Pat. No. 4,826,673, U.S. Pat. No. 4,639,365, EP-A-71564, EP-A-165728, EP-A-232751, EP-A-230893, EP-A-292689, EP-A-287465, DE-A-3633245, DE-A-3324235, EP-A-250358, EP-A-263059, EP-A-173163, EP-A-255471, U.S. Pat. No. 4,687, 659, WO-A-86/02005, WO-A-87/02893, WO-A-85/05554, WO-A-87/01594, WO-A-87/06229, WO-A-90/08138 and WO-A-90/08134.

Several such chelates are inherently site-specific (e.g. the hepatobiliary contrast agents of EP-A-165728). Otherwise chelating moieties may be attached to macromolecular carriers to yield site-specific contrast agents the site specificity of which derives primarily from the nature of the macromolecule. Thus, for example, by coupling chelating moieties to physiologically relatively inert high molecular weight (e.g. greater than 40 KD) dextrans, a blood pool agent may be produced (see EP-A-186947). Alternatively chelating moieties may be coupled directly or indirectly, e.g. via a polymer linker such as polylysine or polyethyleneimine, to biologically active molecules, such as monoclonal antibodies etc., thereby producting a tissue- or organ-targeting contrast agent.

Particulate contrast agents, if administered into the cardiovascular system, will tend to be abstracted by the reticuloendothelial system and thus are particularly suited for use in imaging the liver.

One form of particulate EII contrast agent which may be used according to the invention comprises magnetically locatable particles, especially ferromagnetic, ferrimagnetic and in particular superparamagnetic particles. Such particles have been proposed for use as MRI contrast agents and generally are metallic or are of magnetic metal oxides, e.g. ferrites.

Particlar mention in this regard may be made of the superparamagnetic contrast agents proposed for use as MRI contrast agents by Jacobsen et al. in U.S. Pat. No. 4,863,716, by Klaveness et al. in WO-A-89/11873, by Schrader et al. in WO-A-85/02772, by Groman in WO-A-88/00060, by Schering in EP-A-186616, by Widder et al. in AJR 148:399–404 (1987), by Hemmingsson et al. in Acta Radiologica 28:703–705 (1987), by Hahn et al. in Society of Magnetic Resonance in Medicine, 7th Annual Meeting, 1988, Book of Abstracts, page 738, by Saini et al. in Radiology 162:211–216 (1987), by Clement et al. in CMR89. MR20 (1989), etc.

Superparamagnetic particles, both free and carrier-bound, are widely available and their preparation is described in a large variety of references, e.g. WO-A-83/03920 (Ugelstad), WO-A-89/03675 (Schröder), WO-A-83/03426 (Schröder), WO-A-88/06632 (Josephson), U.S. Pat. No. 4,675,173, DE-A-3508000 and WO-A-88/00060.

The literature contains many suggestions for the formulation of superparamagnetic particles and in particular suggests that the particles can be administered either free (i.e. uncoated and not bound to any other substance) or coated (e.g. dextran coated—see for example U.S. Pat. No. 4,452, 773) or carried by or embedded in a matrix particle (e.g. a polysaccharide—see for example WO-A-83/03920 and WO-A-85/02772) or bound to an organ- or tissue-targeting species, e.g. a biomolecule such as an antibody or a hormone (see for example WO-A-88/00060 and WO-A-88/06632).

Particular mention may also be made of the use of metallic, that is conducting, particles. These may be used as dispersions of free particles but more generally the particles will be coated by or embedded in or on a physiologically tolerable matrix material such as those discussed above. Similarly solutions or dispersions of conducting polymers may also advantageously be used as EII contrast media.

Further examples of particulate contrast media useful as EII contrast media, especially as negative contrast media include the entrapped gas containing particles previously suggested as contrast agents for ultrasound, e.g. Albumex available from Molecular Biosystems Inc, California. Other microbubble or microballoon containing or generating materials, e.g. microvesicles, may also be used.

Particulate contrast agents for parenteral administration should preferably have particle sizes of no more than 1.5 μm, especially 1.0 μm or less.

Other examples of contrast agents which may be used include zeolites and fullerenes, optionally in ionic form and optionally acting as carriers for metal ions. Besides the closed-cage fullerenes, other carbon mesh framework materials such as graphite and the so called "bucky-tubes" may be used as well as their derivatives (e.g. intercalates). Many such materials are known from the literature. Particular reference is made to the disclosures of PCT/EP92/02550 and GB 9203037.8 which are incorporated herein by reference.

Special mention should also be made of biodegradable contrast agents, especially those containing ester or carbonate groups, which break down in vivo to produce ionic groups or to liberate smaller molecular ions, for example by releasing a chelant molecular ion from a macromolecular carrier (which may itself be soluble or particulate). Examples of such biodegradable contrast agents also include certain non-ionic X-ray contrast agents which are pro-drugs for ionic X-ray contrast agents, e.g. ethyl 10-(4-iodophenyl) undecylate and 3,5-diiodo-4-oxo-1(4H) pyridineacetic acid propyl ester. Reference in this regard is also made to the disclosures of JACS 64:1436 (1942), WO-A-89/00988 and WO-A-90/07491.

Non-ionic materials, and ionic compounds with very low charge to mass ratios can be used, if desired, as negative contrast agents especially where high concentrations can be used—as for example in the case with the non-aqueous blood substitutes. However it is also thought possible that at very high frequencies in the impedance measurement even non-ionic compounds may serve to modify the impedance of an aqueous solution. Accordingly the invention does extend to cover the use of non-ionic X-ray contrast agents and non-ionic paramagnetic or diamagnetic metal chelate complexes.

Examples of suitable non-ionic X-ray contrast agents include metrizamide, iopamidol, iohexol, iotrolan, iodecimol, iodixanol, ioglucol, ioglucomide, ioglunide, iogulamide, iomeprol, iopentol, iopromide, iosarcol, iosimide, iotasul, ioversol and ioxilan (see for example DE-A-2031724, BE-A-836355, GB-A-1548594, EP-A-33426, EP-A-49745, EP-A-108638, U.S. Pat. No. 4,314,055, BE-A-846657, DE-A-2456685, BE-A-882309, EP-A-26281, EP-A-105752, DE-A-2909439, DE-A-3407473, DE-A-3001292, EP-A-22056, EP-A-83964 and WO-A-87/00757). Examples of suitable non-ionic MRI contrast agents include Gd-DTPA.BMA, Gd-HP-DO3A, and Dy DTPA.BMA.

Parenteral administration of contrast agents according to the invention will generally be by injection or infusion, especially into the cardiovascular system. However the contrast media may also be administered into body cavities having external voidance ducts, e.g. by catheter into the bladder, uterus etc. Moreover the iodinated contrast agents, the magnetically targetable or electrically conductive contrast agents and the non-radioactive metal chelate contrast agents discussed above may also be used advantageously in EII of the gastrointestinal tract and such use and the use of such materials for the manufacture of EII contrast media for enteral administration constitute further aspects of the present invention.

The dosages of EII contrast media used according to the invention will vary over a broad range depending on a variety of factors such as administration route, the pharmacodynamic properties of the contrast agent (the more widely distributing the agent is the larger the dose may be), the chemical and physical nature of the contrast agent, and the frequency of the electrical current applied in the impedance measurement.

Typically however agents will be administered in concentrations of 1 μmol/l to 1 mol/l, preferably $10^{-2}$ to 10 mmol/l and dosages will lie in the range 0.002 to 20 mmol/kg bodyweight, generally 0.05 to 5 mmol/kg. For matrix bound, carried or encapsulated contrast agents the overall dosage will generally be 1 to 100 ml when administered into the cardiovascular system or 10 ml to 1.5 liters of contrast media when administered into a body cavity having an external voidance duct, e.g. by oral or rectal administration.

Contrast enhanced EII according to the present invention may be performed for a wide range of clinical indications with appropriate selection of the contrast agent (for its pharmacodynamic properties) and of the administration route. Thus non-absorbable EII contrast agents are particularly useful for imaging of the gastrointestinal tract for diagnosis of abnormalities therein or as markers of the gastrointestinal system. Such agents may also be used for dynamic studies, for example of gastric emptying. In studies of the gastrointestinal tract, it may be advisable to use an agent such as cimetidine to suppress naturally occuring pH variations which might otherwise reduce imaging accuracy.

Some of the EII contrast agents are absorbable from the gastrointestinal tract and may be taken up by the liver and excreted into the bile. Such agents can thus be used for imaging the hepatobiliary system and for liver function studies even following oral rather than parenteral administration.

The clinical indications for parenteral EII contrast agents include CNS examination, perfusion studies, blood pool imaging, examination of body cavities, of the pelvic region and of the kidneys, hepatobiliary studies and studies of liver and kidney function, tumour imaging, and diagnosis of infarcts, especially in the heart.

As a further alternative means of improving EII, also within the scope of the invention, contrast may be enhanced by administration of a physiologically active agent which serves to modify body fluid distribution, e.g. a diuretic, thereby causing image modification in body areas where body fluid is increased or decreased.

Besides being useful in electrical impedance tomography, the EII contrast agents mentioned herein may be used for electrical impedance studies of dynamic processes, e.g. blood flow, whether or not actual images are generated. Such use also falls within the scope of the invention.

The invention will now be illustrated further by means of the following non-limiting Examples:

EXAMPLES 1–15

0.01, 0.1 and 1 mmol/l aqueous solutions (or suspensions) of (a) iohexol, (b) metrizoic acid, (c) GdDTPA-BMA, (d) GdDTPA.dimeglumine, and (e) intravenous magnetic particles were prepared and their resistivities at ambient temperature were measured at AC frequencies between 1 and 100 kHz as described in Example 16 below. All showed frequency dependent resistivities of the order of 80 to 3000 $\Omega$.m, generally 500 to 2000 $\Omega$.m, i.e. significantly in excess of the values for most body fluids and soft tissues.

The GdDTPA.BMA samples also contained 5 mol % of the sodium calcium salt of DTPA.BMA; the GdDTPA dimeglumine samples were prepared using commercially available Magnevist (Schering AG); and the intravenous magnetic particles were prepared using the Schröder method as described in Example 7 of WO-A-89/09625.

EXAMPLE 16

Samples of the contrast media of Examples 1 to 16 were placed in a sample holder and resistivity measurements were performed by means of a four-electrode method (illustrated schematically in FIG. 1). AC current with frequency in the range from 1 KHz to 100 KHz was provided through a sweep/function generator model 180 (Wavetek). Sinusoidal signal was chosen. Two DMM model 196 systems (Keithley) were used for measuring AC voltage (RMS). A differential amplifier with imput impedance in $T\Omega$ range was used in measuring the potential difference between C and D (see FIG. 1). The current intensity was measured at each chosen frequency by measuring the voltage across a resistance whose value had been calibrated. With this known current (I) and the magnitude of voltage (V) between the C and D electrodes the resistance (R) of the liquid sample inside the sample holder is given by formula (1)

$$R=V/I \tag{1}$$

The resistivity ($\rho$) of the sample is related to R by formula (2)

$$G(l,s,f) \times \rho = R \tag{2}$$

where $G(l,s,f)$ is a geometric factor which is a function of the distance (l) between the electrodes C and D, the cross-section (s) of the liquid in the sample holder, and the measuring frequency (f). Skin-effects at high frequency AC currents and the uncertainties in the determination of the dimensions of the sample holder, could give rise to significant errors in any direct calculation of $\rho$ using formula (2). Accordingly a liquid sample (a NaCl solution) with a known resistivity was used as a standard sample, and by measuring its resistance, a reference value of $G(l,s,f)$ at each frequency was determined.

I claim:

1. A method of electrical impedance imaging of a human or animal subject which method comprises parenterally administering to said subject an EII contrast agent, optionally dissolved or dispersed in a physiologically tolerable liquid carrier medium and generating an electrical impedance image of at least part of said subject, said contrast agent being capable on dispersion in water of yielding a fluid having an electrical impedance different to that of water and being a physiologically tolerable material wherein said contrast agent is selected from the group consisting of an ionic triiodophenyl group containing compound and a composition comprising membrane encapsulated gas bubbles.

2. A method as claimed in claim 1 wherein said contrast agent comprises a blood pool agent.

3. A method as claimed in claim 1 wherein said contrast agent comprises an ionic triiodophenyl group containing X-ray contrast agent.

4. A method as claimed in claim 1 wherein said contrast agent is sodium diatriazoate.

5. A method as claimed in claim 1 wherein said gas entrapping agent comprises membrane encapsulated gas bubbles.

* * * * *